US 9,566,223 B2
Feb. 14, 2017

(12) United States Patent
Klingman (54) ANTIPERSPIRANTS AND DEODORANTS

(71) Applicant: Shannon Elizabeth Klingman, Chaska, MN (US)

(72) Inventor: Shannon Elizabeth Klingman, Chaska, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/604,733

(22) Filed: Jan. 25, 2015

(65) Prior Publication Data

US 2015/0139927 A1    May 21, 2015

Related U.S. Application Data (63) Continuation of application No. 12/823,834, filed on Jun. 25, 2010, now Pat. No. 8,992,898.

(60) Provisional application No. 61/325,317, filed on Apr. 17, 2010.

(51) Int. Cl.
| | |
|---|---|
| *A61K 8/49* | (2006.01) |
| *A61K 8/73* | (2006.01) |
| *A61K 8/02* | (2006.01) |
| *A61K 8/36* | (2006.01) |
| *A61Q 15/00* | (2006.01) |
| *A61K 8/365* | (2006.01) |

(52) U.S. Cl.
CPC ........... *A61K 8/4953* (2013.01); *A61K 8/0229* (2013.01); *A61K 8/365* (2013.01); *A61Q 15/00* (2013.01); *A61K 8/732* (2013.01); *A61K 2800/74* (2013.01); *A61K 2800/874* (2013.01)

(58) Field of Classification Search
CPC .... A61K 8/365; A61K 8/4953; A61K 8/0229; A61K 8/732; A61K 2800/874; A61Q 15/00
See application file for complete search history.

(56) References Cited

U.S. PATENT DOCUMENTS

| | | | |
|---|---|---|---|
| 2,800,457 A | 7/1957 | Green | |
| 2,857,315 A | 10/1958 | Teller | |
| 2,900,306 A | 8/1959 | Slater | |
| 2,933,433 A | 4/1960 | Teller et al. | |
| 3,116,206 A | 12/1963 | Carl | |
| 3,167,602 A | 1/1965 | Itzhak | |
| 3,202,533 A | 8/1965 | Sachsel | |
| 3,429,827 A | 2/1968 | Ruus | |
| 3,016,308 A | 1/1969 | Macaulay | |
| 3,576,776 A | 4/1971 | Muszik et al. | |
| 4,025,615 A | 5/1977 | Rubino | |
| 4,078,050 A | 3/1978 | Hart | |
| 4,252,789 A | 2/1981 | Broad | |
| 4,490,313 A | 12/1984 | Brown | |
| 4,708,874 A | 11/1987 | De Haan et al. | |
| 4,820,521 A | 4/1989 | Panoz et al. | |
| 5,030,451 A | 7/1991 | Trebosc | |
| 5,091,171 A | 2/1992 | Yu et al. | |
| 5,443,569 A | 8/1995 | Uehira | |
| 5,523,090 A | 6/1996 | Znaiden et al. | |
| 5,650,143 A | 7/1997 | Bergmann | |
| 5,662,937 A * | 9/1997 | McCuaig ................. | A61K 8/26 424/401 |
| 5,700,484 A | 12/1997 | Chauffard et al. | |
| 5,741,592 A | 4/1998 | Lewis et al. | |
| 5,756,107 A | 5/1998 | Hahn et al. | |
| 5,756,136 A | 5/1998 | Black et al. | |
| 5,813,576 A | 9/1998 | Iizuka et al. | |
| 5,888,486 A | 3/1999 | Steinberg | |
| 5,911,923 A | 6/1999 | Work et al. | |
| 5,932,619 A | 8/1999 | Zaneveld et al. | |
| 6,294,161 B1 | 9/2001 | Hiramoto et al. | |
| 6,511,243 B2 | 1/2003 | Miranda | |
| 6,777,224 B2 | 8/2004 | Mitsuhashi et al. | |
| 6,818,204 B2 | 11/2004 | Lapidus | |
| 6,835,397 B2 | 12/2004 | Lee et al. | |
| 6,960,354 B1 | 11/2005 | Leigh et al. | |
| 7,550,200 B2 | 6/2009 | Hart et al. | |
| 2006/0115441 A1 | 6/2006 | James et al. | |
| 2007/0172440 A1 | 7/2007 | Schulz et al. | |
| 2007/0270732 A1 | 11/2007 | Levin et al. | |
| 2008/0299220 A1 | 12/2008 | Tamarkin et al. | |
| 2009/0093440 A1 | 4/2009 | Murad | |
| 2011/0144209 A1 | 6/2011 | Zachar | |

FOREIGN PATENT DOCUMENTS

| | | | | |
|---|---|---|---|---|
| CA | 1085299 A1 * | 9/1980 | ............. | A01N 37/36 |
| CN | 1121222 C * | 9/2003 | | |
| EP | 1175165 B1 | 4/2005 | | |
| WO | WO00/048986 A2 | 8/2000 | | |
| WO | WO02/003952 A2 | 1/2002 | | |
| WO | WO2006/007991 A1 | 1/2006 | | |
| WO | WO 2008049650 A1 * | 5/2008 | ........... | A61K 8/0229 |

OTHER PUBLICATIONS

Liu, CN1277016 (a suitable English translation of CN 1121222 C as a patent family document), Espacenet, downloaded 2015.*
WO 2008049650 A1 English translation, Google Translate, downloaded 2015.*
CA 1085299 A1 Claim set in English, CIPO website, downloaded 2015.*
C. Exley, "Does Antiperspirant Use Increase the Risk of Aluminium-Related Disease, Including Alzheimer's Disease?," Molecular Medicine Today 4 (3): 107-9 (Mar. 1998).
K.G. McGrath, "An Earlier Age of Breast Cancer Diagnosis Related to More Frequent Use of Antiperspirants/Deodorants and Underarm Shaving," European Journal of Cancer Prevention, 12 (6): 479-85 (Dec. 2003), available online at http://www.cbsnews.com/htdocs/pdf/KGM_paper.pdf.
P.D. Darbre, "Underarm Antiperspirants/Deodorants and Breast Cancer," Breast Cancer Research 11 (Suppl 3):S5 (2009),http://www.ncbi.nlm.nih.gov/pmc/articles/PMC27976851?tool=pmcentrez.
Unknown, "Health Conditions: Body Odor," Health 911, http://www.health911.com/remedies/rem_bodyo.htm, 2015.
Cynthia S., "How to Stop Heavy Perspiration," Ezine Articles, http://ezinearticles.com/?How-to-Stop-Heavy-Perspiration&id=608249, 2015.

(Continued)

*Primary Examiner* — Mark V Stevens
(74) *Attorney, Agent, or Firm* — Jeffrey Dean Lindsay (57) ABSTRACT

Products and methods are disclosed for reducing the production of unwanted odors on the human body.

20 Claims, 4 Drawing Sheets

(56) References Cited

OTHER PUBLICATIONS

Unknown, "Are you a pro when it comes to antiperspirant?," DryIdea.com, http://www.dryidea.com/myth-busters (replaces http://www.dryidea.com/dryidea/index.cfm?page_id=7 as cited in the specification), 2015.
Unknown, "Polyolprepolymers: Properties and Use in Cosmetic Products—Technical Manual," Bertek Pharmaceuticals a subsidiary of Mylan Laboratories (Englewood Cliffs New Jersey), 1996.
Unknown, "Polyolprepolymers—Treatment," Barnet Products Corporation, Englewood Cliffs NJ, 2008.
Unknown, "CapsuDar® Caffeine 85," Lycored.com, LycoRed Bio Ltd., Yavne, Israel, Dec. 2008.
Unknown, "Dermalogica Medibac Oil Control Lotion (59ML)," LookFantastic.com, .accessed May 28, 2010.
Erin, "Can Caffeine Give Skin a Lift? ShopSmart Investigates," MakeHerUp.com, http://www.makeherup.com/2009/06/01/can-caffeine-give-skin-a-lift-shopsmart-investigates/, accessed May 28, 2010.
Stevie, "Don't Stress Because It's the Pits!," FashionTribes Daily, http://fashiontribes.typepad.com/beautybuzz/2005/07/dont_ stress_bec.html, Jul. 22, 2005, accessed Sep. 9, 2010.
Schmitt et al. (Tetrahedron Letters, 2009, vol. 50, pp. 3185-3188).
Daly, Cellular and Molecular Life Sciences, 2007, vol. 64, pp. 2153-2169.
Campa et al., Food Chemistry, 2005, vol. 93, pp. 135-139.
Kitzberger et al., Method for Determination of Carboxylic Acids in Green Coffee Beans by RP-HPLC, 2012.
Bradbury et al., Journal of Agriculture and Food Chemistry, 1990, vol. 38, pp. 389-392.
A.J. Seegers et al., "The anti-inflammatory, analgesic and antipyretic activities of non-narcotic analgesic drug mixtures in rats," Archives Internationales Pharmacodynamie et Therapie, 251/2 (Jun. 1981):237-254; http://www.ncbi.nlm.nih.gov/pubmed/6974544, accessed Mar. 16, 2016.
Google Translate screen for the Chinese term for phenacetin, translate.google.com, accessed Mar. 26, 2016.

* cited by examiner

ANTIPERSPIRANTS AND DEODORANTS

CLAIM TO PRIORITY

This application claims priority to U.S. patent application Ser. No. 12/823,834, "Antiperspirants and Deodorants," filed Jun. 25, 2010, which claims priority to U.S. Patent Appl. Ser. No. 61/325,317, "Improved Antiperspirant," filed Apr. 17, 2010, both of which are hereby incorporated by reference in their entirety for all purposes.

BACKGROUND

Field of the Invention

This invention pertains to products and methods for personal care, particularly personal care compositions and methods of use for reducing or preventing unwanted perspiration or odor associated with perspiration.

Description of Related Art

Many people seek to avoid the embarrassment or discomfort associated with perspiration or associated odors. Bacteria such as Corynebacteria feed off materials in the sweat, particularly the apocrine sweat glands found under the arms and elsewhere, and produce unpleasant odors. Many people purchase antiperspirants or deodorants for underarm use, for example, to mask odors or reduce perspiration.

Unfortunately, the metal-containing compounds such as aluminum salts that are widely used for their ability to reduce perspiration have been the subject of as-yet unresolved concerns about their long-term health effects. Some people are allergic to aluminum and may suffer contact dermatitis after using aluminum-containing antiperspirants. Some reports have linked aluminum-containing antiperspirants with the systemic accumulation of aluminum in the body, which may be a risk factor for Alzheimer's disease or breast cancer. See, for example, C. Exley. "Does Antiperspirant Use Increase the Risk of Aluminium-Related Disease, Including Alzheimer's Disease?," *Molecular Medicine Today* 4 (3): 107-9 (March 1998); K. G. McGrath K G, "An Earlier Age of Breast Cancer Diagnosis Related to More Frequent Use of Antiperspirants/Deodorants and Underarm Shaving," *European Journal of Cancer Prevention,* 12 (6): 479-85 (December 2003); and P. D. Darbre, "Underarm Antiperspirants/Deodorants and Breast Cancer," Breast Cancer Research 11 (Suppl 3):S5(2009), http://www.ncbi.nlm.nih.gov/pmc/articles/PMC2797685/?tool=pmcentrez.

Such compounds are also capable of staining clothing, often leading to an unwanted yellowness on white fabric, for example. Such aluminum-based compounds include ammonium zirconyl compounds such as those described in U.S. Pat. No. 4,025,615, issued May 24, 1977 to Rubino, and U.S. Pat. No. 5,888,486 issued Mar. 30, 1999 to Steinberg and O'Lenick; both of which are herein incorporated by reference to the extent that they are noncontradictory herewith.

Efforts to provide aluminum-free deodorants for underarm use include products with synthetic antibacterial agents such as Triclosan, which at high levels have prompted concerns by some groups. Bacterial inhibition has also been attempted with botanical ingredients such as *Phellodendron Amurense* Bark Extract which is said to help inhibit sweat-induced odor. However, both synthetic and bio-derived ingredients previously used for this purpose may cause irritation of the skin or may not provide other beneficial properties with respect to skin and hair in the region of application.

Given the limitations in currently available products, there is a need for deodorants and antiperspirants that are effective in preventing perspiration or associated odor on the body, while reducing perceived health risks associated with aluminum compounds or other harsh chemicals.

As used herein, "deodorants" and "antiperspirants" both refer to compositions that are effective in directly or indirectly reducing unwanted body odors associated with perspiration and/or bacteria on the surface of the skin. "Deodorants" may reduce odor through a variety of means, and such means in the various embodiments of the present invention may include suppression of bacterial activity, antimicrobial mechanisms, chemical interference with odor generation mechanisms, removal or modification of feedstuff for odor-producing bacteria, and the like. "Antiperspirants" generally work to reduce the production of perspiration, and may do so, for example, by decreasing the size of pores associated with sweat glands, blocking sweat glands, reducing the flow of blood or other fluids to sweat glands, and the like. A deodorant may function as an antiperspirant but need not do so to be a deodorant. The compositions of various embodiments of the present invention may generally be described as deodorants and in many cases may generally be described as antiperspirants, though a composition that has limited antiperspirant efficacy is not necessarily outside the scope of the claimed invention, which is defined by the claims appended hereafter.

SUMMARY

We have found that personal care compositions comprising caffeine can provide highly effective protection against perspiration without the need to use aluminum compounds. We have also found that deodorant formulations comprising caffeine (a methylxanthine) or related xanthines can be used to reduce perspiration and/or odor. In several embodiments, the xanthine compound is combined with alpha-hydroxy acids such as relatively non-irritating mandelic acid to significantly reduce body odor in regions of the body such as the underarm region normally subject to undesirable odors associated with perspiration. Thus, in one embodiment, we have developed a personal care composition for reducing at least one of perspiration and body odor comprising an effective amount of a xanthine compound and at least 0.5% by weight of a carboxylic acid in a suitable carrier for application to the skin. In another aspect, we have developed an antiperspirant for use on human skin comprising about 1% by weight or greater of a xanthine compound in a suitable carrier. In yet another aspect, we have developed an effective antiperspirant composition comprising at least 1% caffeine, at least 1% mandelic acid, at least 5% starch, and substantially no aluminum or zirconium compounds. Further, we have developed a method of making a substantially aluminum-free personal care composition comprising blending caffeine, an alpha-hydroxy acid, and a suitable carrier to form a viscous composition, and packing the composition in a container with indicia associated therewith instructing a user to apply the composition to the underarms region or other region of the body likely to experience body odor associated with sweat.

The discovery of the surprising efficacy of such formulations initially stemmed from surprising discoveries regarding the role of mandelic acid and related carboxylic acids in suppressing odor generation on the body, as described in commonly owned US patent applications 61/289,992, "Products and Methods for Reducing Malodor from the Pudendum," filed Dec. 23, 2009, and 61/309,831, "Products and Methods for Reducing Malodor from the Pudendum," filed Mar. 2, 2010, both by Shannon Klingman, the disclosures of both of which are herein incorporated by reference, and from other experimental discoveries regarding the surprising benefits of topically applied caffeine in reducing underarm odor, alone or in combination with alpha-hydroxy carboxylic acids.

Caffeine is known to increase perspiration and is said to increase body odor when consumed (see, for example, http://www.health911.com/remedies/rem_bodyo.htm, accessed May 28, 2010, http://ezinearticles.com/?How-to-Stop-Heavy-Perspiration&id=608249 and http://www.dry-idea.com/dryidea/index.cfm?page_id=7 under the heading, "MYTH: When I Eat Garlic, My Sweat Smells Like Garlic," both accessed Mar. 30, 2010). Given its apparent role in increasing perspiration and body odor, the discovery that caffeine can, when properly applied to the body, actually serve to reduce body odor and/or to reduce perspiration is counterintuitive. The synergy between caffeine and related compounds with carboxylic acids such as mandelic acid in reducing body odor from perspiration is also highly surprising relative to the state of understanding before the advances described herein. However, upon discovery of these surprising effects, a theory for the surprising efficacy can be proposed with hindsight by consideration of the ability of caffeine to restrict blood vessels in the skin.

Without wishing to be bound by theory, we propose that a vaso-restrictive function of caffeine when topically applied helps to close pores rather than plugging them (as in certain prior antiperspirant products) with the reaction products of metal complexes with biological matter. The closing of sweat-releasing pores through the action of caffeine is believed to help reduce the flow of sweat from sweat glands, thus providing an antiperspirant function. Alternatively or in addition, the caffeine can act to reduce blood flow to the surface of the skin, and it is possible that the reduced blood flow works to reduce sweat production from sweat glands. Alternatively, mechanisms that reduce blood flow may also work to reduce the supply of perspiration available in or deliverable by sweat glands via similar mechanisms.

Caffeine and other vasoconstrictors or chemically related compounds may be used in the formulations of the present invention, including xanthine derivatives. Caffeine is a methylxanthine (a derivative of xanthine having a methyl group). Xanthine (3,7-dihydro-purine-2,6-dione), is a purine base found in most human body tissues and fluids and in other organisms.

In forming a deodorant formulation, the caffeine or other xanthines may be provided as a solute in an aqueous solution, a non-aqueous solution in combination with an alcohol or other liquid, an emulsion, a mixture of encapsulated ingredients such as microencapsulated caffeine in combination with ingredients in one or more phases, or in other suitable forms. Emulsions, if used, can be oil in water emulsions or water in oil emulsions, for example. Water-in-water emulsions, such as gel particles in an aqueous phase, may also be considered, with the xanthine distributed in either or both phases. The caffeine or other xanthines may also be provided in solid form, such as in the form of a powder. Either solid or solute forms of one or mores xanthines may be encapsulated. For example, microcapsules of caffeine may be prepared with capsule walls that are at least one of (a) water-soluble, (b) fusible (e.g., melting above a predetermined temperature such as at about 95° F. or higher), or (c) frangible (such that they can break in response to friction to release the contained ingredients).

Encapsulating materials (the material used to form the wall of, say, a microcapsule containing a xanthine, for example) can include any known in the art, including, for example, gelatin and derivatives thereof, melamine compounds (including combinations of melamine and polyacrylic acid), polyvinyl alcohol compounds, polyurethanes, waxes, acrylates, sodium caseinate, other proteinaceous or bio-derived materials and the Encapsys® encapsulation materials marketed by Appleton Papers (Appleton, Wis.), as well as all combinations or derivatives thereof. One or more active ingredients may also be provided in a microsponge, zeolites, cyclodextrin complex, gel, polymer complex, or other medium for controlled release or time-release functionality. Exemplary commercial products include CapsuDar® Caffeine 85, a microencapsulated free flowing caffeine powder coated with cellulose derivative, marketed by LycoRed Bio Ltd. (Yavne, Israel).

Preparation of encapsulated caffeine or other components may be performed using the technologies and services of other entities such as, for example, Maxx Performance Inc. (Chester, N.Y.), Appleton Papers (Appleton, Wis.), or 3M (Minneapolis, Minn.), including technologies described in U.S. Pat. No. 2,800,457, "Oil-Containing Microscopic Capsules and Method of Making Them," issued to B. K. Green and S. Lowell, Jul. 23, 1957. Other methods of encapsulation include those described in the following US patents, each of which is herein incorporated by reference to the extent it is non-contradictory herewith: U.S. Pat. Nos. 3,016,308; 3,116,206; 3,167,602; 3,202,533; 3,429,827; 4,490,313; and 5,741,592.

The microencapsulation technologies of Microtek Laboratories (Dayton, Ohio), particularly those for aqueous solutions, may also be considered, including hydrolyzed polyvinyl alcohols, phenolic resins (e.g., urea-rescorcinol-formaldehyde), urethane coacervates such as the reaction products of an isocyanate and a diol or polyol, and the systems described in U.S. Pat. No. 7,550,200, "Microencapsulation of Biocides and Antifouling Agents," issued Jun. 23, 2009 to Hart et al.; and U.S. Pat. No. 5,911,923, "Method for Microencapsulating Water-Soluble or Water-Dispersible or Water-Sensitive Materials in an Organic Continuous Phase," issued Jun. 15, 1999 to Work, et al., both of which are herein incorporated by reference to the extent that they are noncontradictory herewith.

Other preparations for sustained release of caffeine or other ingredients are described in U.S. Pat. No. 5,700,484, "Sustained Release Microparticulate Caffeine Formulation," issued Dec. 23, 1997 to Chauffard et al.; U.S. Pat. No. 4,708,874, "Devices for the Controlled Release of Active Substances, as Well as Process for the Preparation Thereof," issued Nov. 24, 1987 to De Haan et al.; and U.S. Pat. No. 4,820,521, "Sustained Absorption Pharmaceutical Composition," issued Apr. 11, 1989 to Panoz et al.; all of which are herein incorporated by reference to the extent that they are noncontradictory herewith.

Other xanthines are also believed or known to have vasoconstrictive effects relative to the skin or other potentially useful effects relative to antiperspirant and deodorant products, including pharmacological effects related to those of caffeine, and thus xanthines such as methylxanthines and derivatives thereof are considered within the scope of certain embodiments of the present invention. Methylxanthines include theophylline (1,3-dimethyl-7H-purine-2,6-dione, also known as dimethylxanthine), caffeine (1,3,7-trimethyl-1H-purine-2,6(3H,7H)-dione, also known as 1,3,7-trimethylxanthine or methyltheobromine), and theobromine (3,7-dimethyl-2,3,6,7-tetrahydro-1H-purine-2,6-dione, also known as 3,7-dimethylxanthine or xantheose). Derivatives of xanthine compounds including salts thereof may be used, including caffeine citrate and other salts with carboxylic acids.

Xanthine-containing herbs include *Camellia sinensis* (Tea), *Coffea arabica* (Coffee beans), *Cola nitida* (Kola), *Cola acuminata*, *Theobroma cacao* (Cacao), *Theobroma bicolor*, *Theobroma angustifolium*, *Ilex paraguariensis* (Maté), *Paullinia cupana* (Guarana), *Banisteriopsis inebrians*, *Davilla rugosa*, *Euonymus europaeus*, *Erodium* spp., *Genipa* spp., *Lippia multiflora*, *Maytenus* spp., *Sterculia* spp., *Tylophora mollissima*, the Yaupon Holly (*Ilex vomitoria*) and *Villarsia* spp. The xanthine compound may be provided via a plant extract or mixture of plant extracts. In one embodiment, the composition comprises an herbal extract which has been substantially enriched in xanthine content beyond that available by forming an extract with heated water or ethanol alone. In one embodiment, for example, substantially pure caffeine and a xanthine-containing plant extract are combined to form a personal care composition with deodorant and/or antiperspirant properties.

In some embodiments, the caffeine or other xanthine compound may be present at any effective concentration such as about 10% by weight or higher, about 5% by weight or higher, about 2% by weight or higher, about 1% by weight or higher, or about 0.5% or higher. If a carboxylic acid such as mandelic acid or a mixture of alpha-hydroxy acids, it may be present at any effective concentration such as about 10% by weight or higher, about 5% by weight or higher, about 2% by weight or higher, or about 1% by weight or higher, or about 0.5% or higher. The mass ratio of carboxylic acid to total xanthine compounds may be substantially zero or any practical finite number such as from about 0.1 to about 5.0, from about 0.1 to about 1, from about 0.1 to about 0.5, or from about 1 to about 5, or substantially greater than 1 such as about 1.2 or greater.

Without wishing to be bound by theory, the role of mandelic acid or other suitable carboxylic acids is believed to be that of an acidifying composition that reduces the pH of the skin to a level that limits the growth of the bacteria that produce undesirable odors. Such bacteria can include Corynebacteria and Propionobacteria that dwell on the skin. In addition or alternatively, the reduced pH creates an environment that protects or maintains healthy microbial flora on the skin, thereby controlling the levels of less desirable bacteria that may produce unwanted odors.

The xanthine compound and carboxylic acid (the "active ingredients" as used herein) in many embodiments are combined with a carrier that may be a liquid such as an aqueous solution, a wet wipe formulation with alcohol or substantially alcohol free, or a viscous carrier having substantially greater viscosity than water. The viscous carrier may be a lipophilic carrier such as a mineral oil, a gel, a cream, an emulsion, a bioadhesive, and the like.

The active ingredients may be combined with additional ingredients such as organic oils, silicone compounds, cyclomethicone, water, various polymers that control viscosity, film formation, or other mechanical or fluid properties, fragrances, coloring agents, encapsulated compounds, solvents, propellants, surfactants, and the like. For example, an antiperspirant may comprise caffeine or related compounds in a base made with a starch with bonding agents such as a wax or oil. In another embodiment, the antiperspirant may comprise active ingredients such as caffeine and an acidifying agent such as a carboxylic acid combined with a silicone wax, cyclomethicone, and a fatty alcohol according to the carrier materials discussed in U.S. Pat. No. 5,888,486, previously incorporated by reference.

Such compositions may be applied to the body in a variety of ways, such as by application using a pretreated wipe, pad, or absorbent article such as a dress pad containing the composition that transfers to the body, or by direct application to the body using a spray or other dispenser or by application using the fingers or other means to apply the composition onto the skin.

Any suitable dispenser and method of application may be considered. In one version, the composition is provided in a flexible, squeezable tube with an opening for release in response to pressure applied to the tube.

The composition may be substantially free of aluminum, aluminum salts, or other aluminum compounds, such as having less than 1%, less than 0.5%, less than 0.1%, or less than 0.01% of aluminum (e.g., aluminum ions). The composition may be substantially free of zirconium, such as having less than 1%, less than 0.5%, less than 0.1%, or less than 0.01% of zirconium (e.g., zirconium ions). In general, the composition may be substantially free of effective amounts of aluminum and zirconium antiperspirant compounds.

DETAILED DESCRIPTION

Figure 1:
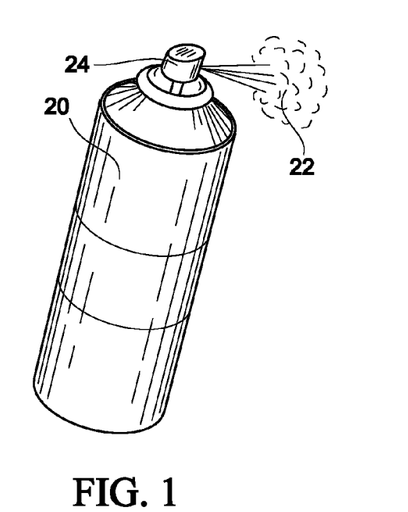
FIG. 1 depicts a spray can comprising a personal care composition according to certain embodiments of the present invention.

FIGS. 1-5 show various dispensers and applicators that can be used to deliver effective quantities of deodorant compositions to the surface of a body. FIG. 1 depicts an aerosol can 20 for dispensing a composition 22 according to certain embodiments of the present invention. The composition 22 is sprayed on the body (not shown) via a manually activated spray nozzle 24, as is known in the art. Any known methods can be used for preparing a suitable solution or suspension for dispensing via aerosol, and any suitable propellants may be used.

Figure 2A:
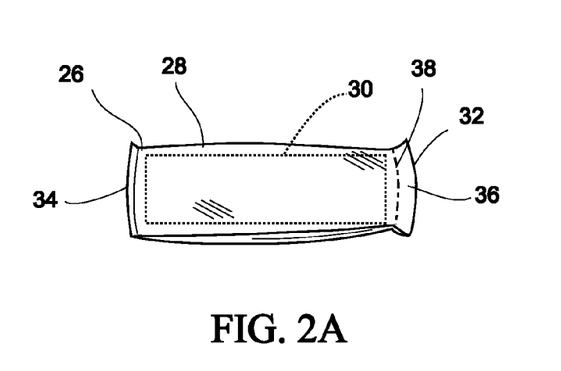
FIGS. 2A and 2B depict a wipe in a pouch according to certain embodiments of the present invention.
Figure 2B:
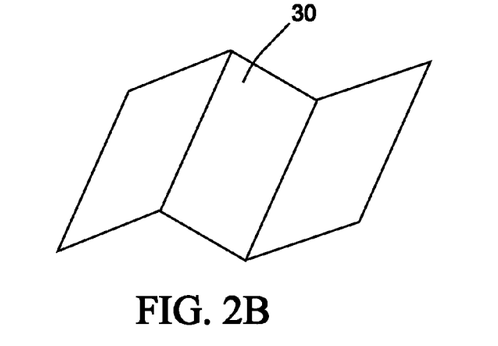

FIGS. 2A and 2B depict a wipe system 26 for applying compositions according to certain embodiments of the present invention. The wipe system 26 comprises an openable pouch 28, which may be a polymeric, foil, paper, or composite pouch, within which is a folded wipe 30 impregnated or coated with a quantity of a deodorant composition comprising a xanthine compound. The unfolded wipe 30 is shown in FIG. 2B. In FIG. 2A, the pouch 28 is shown to have a first end 34 and a second end 36 which may be opened, for example, by tearing the pouch along a tear line 38.

Figure 3:
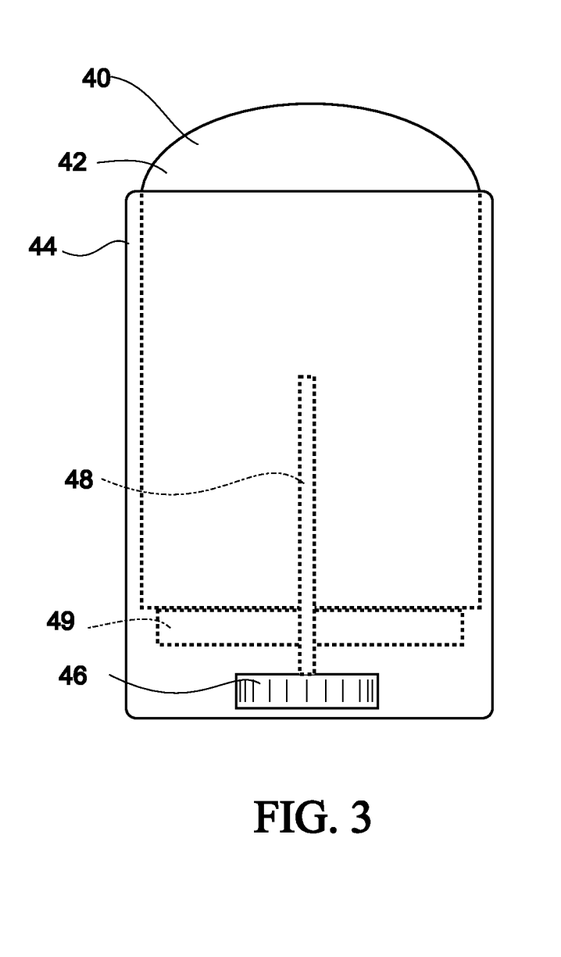
FIG. 3 depicts a stick of deodorant in a dispenser according to certain embodiments of the present invention.

FIG. 3 depicts a stick dispenser 40 comprising a stick of a deodorant composition 42 contained within the walls of a container 44 having a turnable knob 46 attached to a threaded spindle 48 that drives the motion of an associated platform 49 on which the stick of a deodorant composition 42 rests. Thus, by turning the knob 46, the amount of the stick of a deodorant composition 42 rising above the walls of a container 44 can be adjusted. A cap for the container 44 is not shown.

Figure 4:
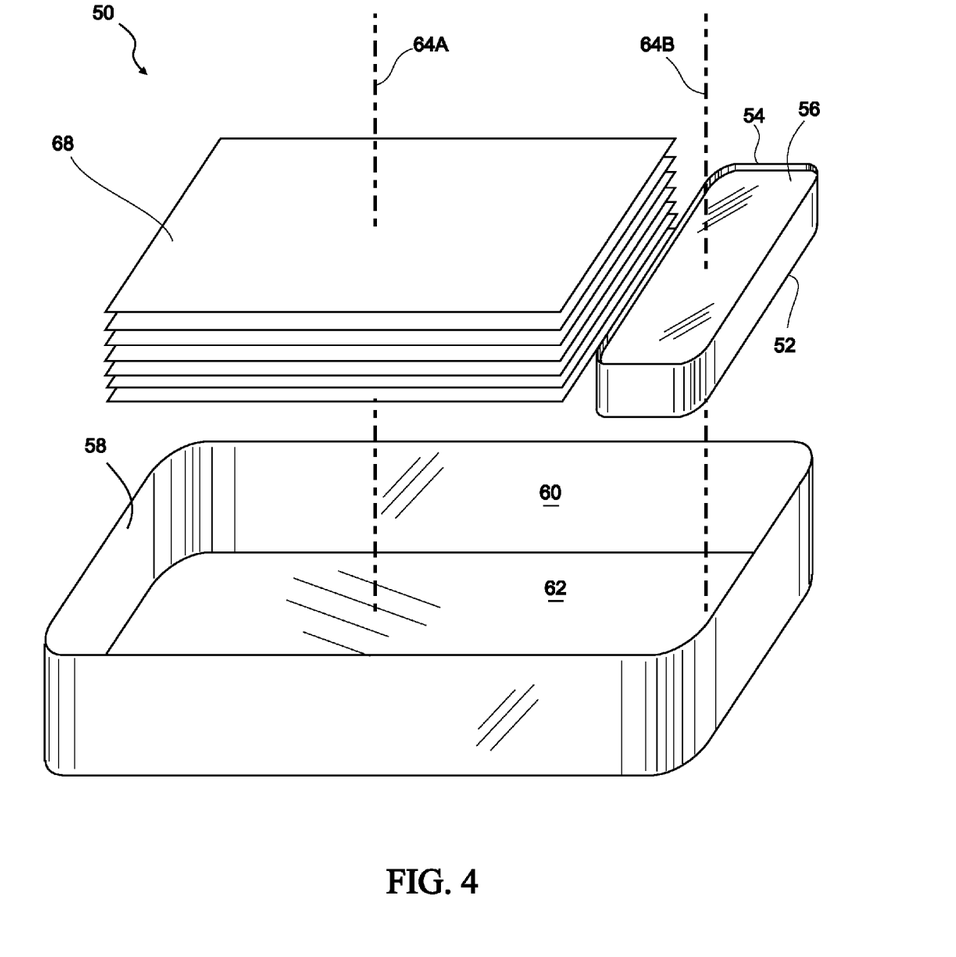
FIG. 4 depicts a portion of a wipes container according to certain embodiments of the present invention.

FIG. 4 shows a telescopic view of a portion of a wipes container 50 showing a lower body 58 adapted to contain a stack of wipes 68 and a deodorant composition dispenser 52 depicted here as a simple well 54 holding a quantity of a deodorant composition 56 comprising a composition in the form of a cream comprising an effective amount of a xanthine composition (e.g., over 1% caffeine). The well 54 may comprise a resilient material such as a polyolefin plastic or may have flexible walls. The well 54 may be separable from the lower body 58 of the wipes container 50 as shown or may be unitary therewith, such as a well 54 formed with the lower body 58 from plastic injection molding (not shown). The deodorant composition dispenser 52, in other embodiments, may be replaced with other known dispensers of formulations, including flexible pouches (not shown) that can release a cream by squeezing, or dispensers with mechanical means for dispensing such as pumps (not shown). The wipes 68 may be used to apply a quantity of the deodorant composition 56 to the underarm region of the body (not shown) or to other regions, as desired.

The lower body 58 has a floor 62 and side walls 60. The lower body 58 receives the stack of wipes 24 as shown along the telescoping axis 64A, and also receives the deodorant composition dispenser 52 along the parallel telescoping axis 64B.

A covering for the container 50 is not shown, but any known covering may be used such as a removable lid or a hinged lid connected to or integral with the lower body 58. In use, the covering (not shown) may be opened to allow a user to remove a wipe 68, apply a quantity of the deodorant composition 56 to the wipe 70, and then apply the wipe to the body.

Figure 5:
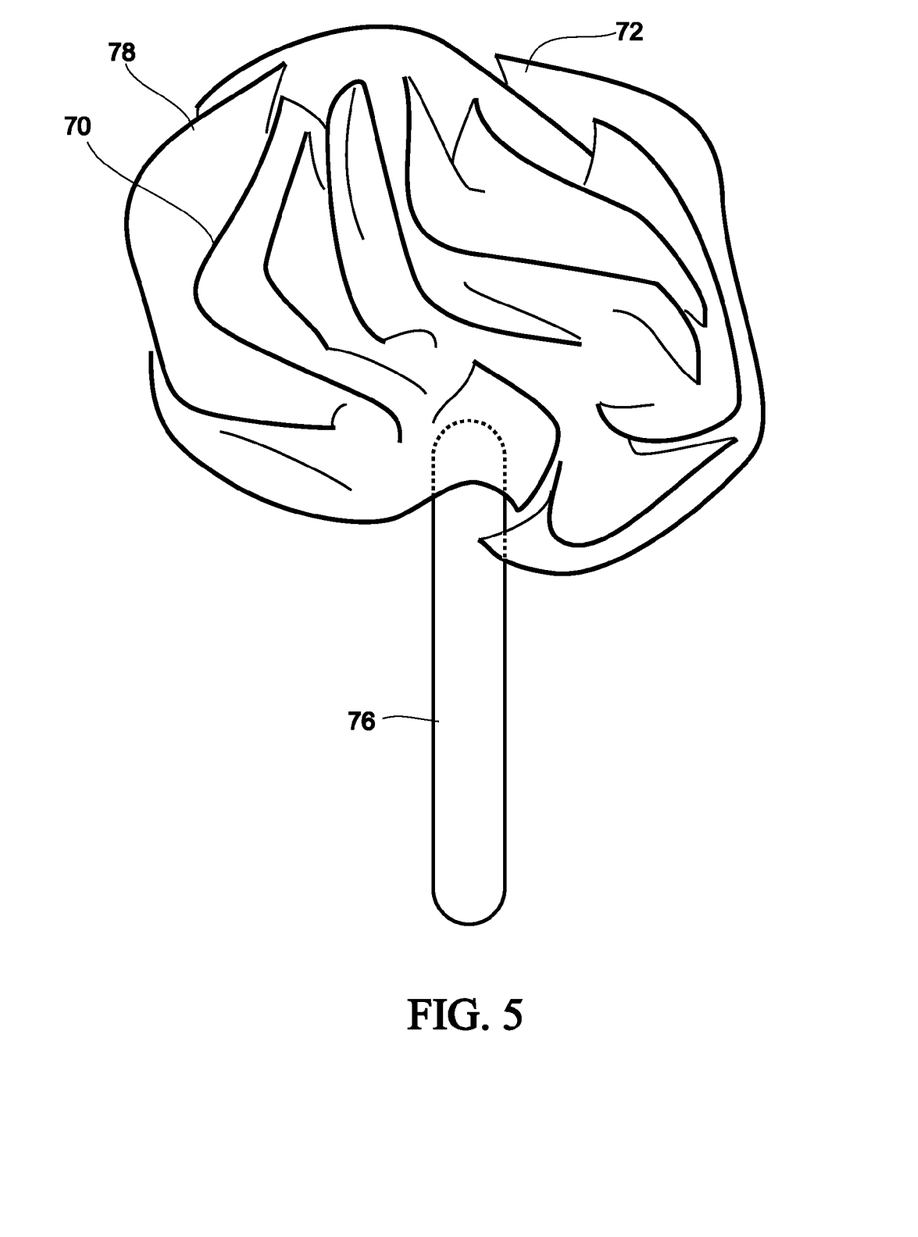
FIG. 5 depicts another applicator for compositions according to certain embodiments of the present invention.

FIG. 5 depicts a flexible "puff" applicator 70 which can be dipped into a container of a deodorant composition (not shown, but see FIG. 4 for an example) comprising a xanthine according to various embodiments of the present invention. The applicator 70 may comprise a handle 76 such as a wooden or plastic stick to which is attached a flexible applicator head 78 that may, for example, comprise one or more pleated or folded sheets 72 of a flexible material such as silicone, a plastic web such as a nylon or polypropylene mesh, a textile such as a nonwoven fabric, and the like. The applicator 70 may thus be used to apply the deodorant composition onto the body (not shown).

Further Details

Caffeine or related xanthines may be provided as pure substances, as phytoextracts, or in combination with other useful ingredients, and then blended with other suitable ingredients for the desired product form to give an antideodorant or antiperspirant product. In some embodiments, the sweat inhibitory effect of caffeine or related xanthines is enhanced with antimicrobial benefits from carboxylic acids, particularly alpha-hydroxy carboxylic acids such as mandelic acid or derivatives thereof.

References to caffeine or any other xanthine are understood to include salts thereof. Thus, caffeine citrate is understood to fall within the scope of caffeine, although for purposes of computing the weight percent of caffeine when a caffeine salt is present, the mass of the salt should be normalized to the effective mass of pure caffeine that would be present if the caffeine were not in salt form. The same principle applies to other xanthines as well.

Formulation may be achieved by any known means for preparing a composition of a desired format (e.g., cream, roll-on, spray, etc.). This may include heating, agitating, homogenizing, pressurized extrusion, and the like, with batch, continuous, or semi-continuous processing all being within the scope of the methods for various embodiments of the present invention.

As used herein, the term "alpha-hydroxy acid" refers to compounds represented by the following generic structure:

(R1)(R2))C(OH)COOH where R1 and R2 are H, alkyl, aralkyl or aryl groups. In addition, R1 and R2 may carry OH, CHO, COOH and alkoxy groups. Typical alkyl, aralkyl and aryl groups for R1 and R2 include methyl, ethyl, propyl, isopropyl, butyl, pentyl, octyl, lauryl, stearyl, benzyl and phenyl etc. The alpha-hydroxy acids include, but are not limited to, lactic acid, mandelic acid, glycolic acid, malic acid, 2-hydroxyoctanoic acid, 2-hydroxydecanoic acid, and citric acid. In some embodiments, the alpha-hydroxy acid has 13 or fewer carbons, 12 or fewer carbons, 11 or fewer carbons, 10 or fewer carbons, 9 or fewer carbons, or 8 or fewer carbons, such as between 2 and 14 carbons, between 2 and 11 carbons, between 3 and 11 carbons, between 3 and 13 carbons, between 7 and 12 carbons, or between 8 and 12 carbons. In one embodiment, the alpha-hydroxy acids comprise a mixture of 3-carbon and 8-carbon alpha-hydroxy acids.

The formulation may include a first alpha-hydroxy acid such as mandelic acid (also known as phenylglycolic acid) and optionally a second alpha-hydroxy acid composition such as lactic acid and/or other carboxylic acids, including acids such as citric, glycolic, 2-hydroxybutyric acid, tartaric acid; gluconic acid or other isomers of pentahydroxyhexanoic acid; hydroxycaprylic acid, leucic acid (2-hydroxy-4-methylpentanoic acid), ethylglycolic acid, malic acid, and the like. U.S. Pat. No. 5,091,171, "Amphoteric Compositions and Polymeric Forms of Alpha Hydroxyacids, and Their Therapeutic Use," issued February, 1992 to Yu et al., herein incorporated by reference to the extent that it is noncontradictory herewith, describes alpha hydroxyl acids that can be considered for use with various embodiments of the present invention. The first alpha-hydroxy acid may have at least 7 or at least 8 carbons for each carboxylic acid group and may have a molecular weight from about 135 to about 400, more specifically from about 135 to about 250, from about 135 to about 200, or from 145 to 170. The first alpha-hydroxy acid may be monoprotic (a monocarboxylic acid) or, in some versions, diprotic (a dicarboxylic acid), though larger numbers of carboxylic acid groups may be considered. In other versions, the first alpha-hydroxy acid or both the first and second alpha-hydroxy acid may have a molecular weight of 90 or greater, 100 or greater, 120 or greater, 150 or greater, or 160 or greater. The first alpha-hydroxy acid also may have at least one aromatic ring such as a phenyl group. (Mandelic acid is the smallest alpha hydroxy acid with an aromatic ring.) Without wishing to be bound by theory, it is believed that the first alpha-hydroxy acid as described is large enough to not rapidly penetrate into the stratum corneum of the skin, allowing it to remain present and active on the surface of the skin for a prolonged period of time, while it is also small enough to be biologically active to modify the bacterial environment on the skin and/or to maintain an acidic condition on the surface of the skin. The relatively high molecular weight and larger number of carbons per acid group in such acids may also reduce the potential for irritation to the skin.

In some embodiments, other alpha-hydroxy acids comprising aromatic rings may be used, including derivatives of mandelic acid such as those described in U.S. Pat. No. 6,777,224, "Method for Producing Optically Active Mandelic Acid Derivatives," issued Aug. 17, 2004 to Mitsuhashi et al., or the dimmers and other derivatives described in U.S. Pat. No. 5,932,619, "Method for Preventing Sexually Transmitted Diseases," issued Aug. 3, 1999 to Zaneveld et al., both of which are herein incorporated by reference to the extent that they are noncontradictory herewith.

The second alpha-hydroxy acid composition may, in some embodiments, help improve the efficacy of the first alpha-hydroxy acid while also contributing to desired acidity on the skin and optionally may also have an antimicrobial effect relative to unwanted bacteria that otherwise could contribute to an undesired odor. The second alpha-hydroxy acid composition may comprise alpha-hydroxy acids having, individually or averaged, a molecular weight of about 170 or less, such as from 75 to 135, from 75 to 125, or from 80 to 85, or from 86 to 92.

The alpha-hydroxy acids in total may be present in any suitable concentration, such as 30% by weight or less, 20% by weight or less, or 10% by weight or less, and more specifically from about 0.3% to 10% (percentages in reference to chemical compositions herein will be understood to be weight percent unless otherwise indicated), from about 0.5% to about 6%, from about 1% to about 15%, or from about 0.5% to about 3.5%, or from about 0.1% to about 2.5%.

In one version, the second alpha-hydroxy acid composition comprises at least about 30%, at least about 50%, at least about 70% or at least about 93% lactic acid by weight (i.e., weight percent) of lactic acid, such as from about 30% to about 90%, or from about 50% to about 95%; or from about 50% to about 95% lactic acid by weight. In one version, the second alpha-hydroxy acid is substantially all lactic acid.

Examples of formulations can include lotions, creams, gels, wipe solutions, sprays, powders, etc., with the following acidifying compositions, expressed as weight percents: 1.5% lactic acid and 0.5% mandelic acid; 2.5% lactic acid and 1% mandelic acid; 25% lactic acid and 2% mandelic acid; 10% lactic acid and 10% mandelic acid; 5% lactic acid and 4% mandelic acid; etc.

The alpha-hydroxy acids may, at least in part, be provided in time-release systems that gradually release the alpha-hydroxy acid to be effective in controlling the pH of the skin in a region subject to sweat and body odor such as under the arms. Time-release technology can include microencapsulation and other systems known in the art. Time-release or other controlled release means are well known in the art. Some versions, by way of example, are described in U.S. Pat. No. 5,756,136, "Controlled Release Encapsulation Compositions," issued May 26, 1998 to Black et al.; and U.S. Pat. No. 6,835,397, "Controlled Release Encapsulated Bioactive Substances," issued Dec. 28, 2004 to Lee et al.; both of which are herein incorporated by reference to the extent that they are noncontradictory herewith.

In many embodiments, the formulations and methods disclosed herein avoid the problems of stinging or other forms of irritation that are known in some prior products. Sting-free formulations, for example, may be substantially free of ethanol, propanol, or other agents that may sting the skin, especially freshly shaved skin.

To provide an effective quantity of a suitable alpha-hydroxy acid in the environment on the skin, a viscous carrier substantially more viscous than water can be effective in retaining the material. A lipophilic carrier such as a cream can further protect the skin and reduce risks of irritation from the alpha-hydroxy acid. One or more suitable alpha-hydroxy acids in combination with a viscous lipophilic carrier can be applied to the skin using the fingers or via a wipe or pad, or can be transferred from another article such as the pretreated surface of an absorbent pad.

Formulations within the scope of the present invention may be provided in the form of pre-treated wipes, including wet wipes or wipes pretreated with a viscous lotion, or may be applied to a wipe shortly before contacting the wipe to the skin. In one embodiment, for example, a cream comprising one or more suitable alpha-hydroxy acids is applied to a wipe, including a dry wipe or a wet wipe, prior to use. The wipe may be packaged with the cream already in contact therewith, or may be packaged with or marketed in association with a quantity of the cream that can be manually applied to the wipe prior to contacting the wipe with the skin, such that the cream is transferred to the skin.

The carrier need not be lipophilic and may, for example, comprise an aqueous gel or other aqueous bioadhesive comprise a hydrated polymer. Alternatively, a substantially aqueous, low-viscosity carrier may be used similar to traditional water-based wet wipe formulations, but comprising a suitable alpha-hydroxy acid. For the alpha-hydroxy acid to remain effective on the skin for a prolonged period of time after application with a wet wipe-style product, additional measures may be taken such as encapsulation of at least a portion of a quantity of an alpha-hydroxy acid for sustained release thereof, or providing of delivery means for sustained contact of a low-pH solution with the skin. The means of delivery, the frequency of delivery, the amount delivered, and the extent of the surface area to which the composition is applied can be varied and adapted for the needs of a user. In other words, the delivery means and all aspects of delivery of the composition can be personalized to meet the needs of a user. Various protocols may be prescribed or recommended responsive to user needs and personal data such as gender, age, skin type, nutrition, race, climate, lifestyle, occupation, activity level, humidity, clothing style, etc. Automated computer tools such as interactive websites may be used in making such recommendations, or guide may be provided to assist human staff in making recommendations.

In some embodiments a textured applicator or brush may be provided with the product that can stimulate the skin as the composition is spread or rubbed into the skin. A suitable brush may, for example, resemble a soft plastic nail brush but with relatively short bristles. A terry cloth or textured fabric, nonwoven, or wipe may be used as well. Alternatively, the container for a cream, paste, stick, gel, or other product may have a textured cap or other texture surface that can be used to apply the composition to the skin.

In some versions, the composition with one or more suitable alpha-hydroxy acids is provided in a container or with a kit that contains indicia instructing the user that the composition is to be applied to the skin or to particular regions such as the underarm. The indicia may further specify suggested methods for repeat application, including time intervals or conditions which would require more frequent application. In some versions, the indicia indicate that the product can help control odor and/or reduce perspiration. For example, the indicia may specify that for some users the full antiperspirant effect may require at least daily application (or, for example, twice daily application) for a period of time such as two or more days, three or more days, four or more days, five or more days, or another period of time such as about a week or longer or about two weeks or longer.

The indicia may instruct the user to rub the composition into the skin vigorously to ensure that the composition enters into the follicles for best results.

The indicia may provide directions about the regions of the body where the product can be used most successfully. For example, any region with apocrine glands may be considered, as well as the more widespread eccrine glands that produce sweat less subject to odor problems.

Regions of the body likely to experience unwanted body odor associated with perspiration include regions with apocrine sweat glands such as the underarms region and the groin or pudendum, and may also include other regions such as the chest, under the breasts, the back, the feet, the scalp, and so forth. Such regions may be identified in indicia (not shown) associated with various products based on selected embodiments of the present invention. Areas where body odor from sweat may be less likely include the face or facial skin, the forearms, the hands (especially the back of the hands), and the neck. In some embodiments, application of the deodorant composition to the face may be specifically proscribed (especially to skin near the eyes, nose, or mouth). The same may apply for the back of the hands and the exposed neck. Thus, indicia may indicate that the product should be used in the underarm region or other regions likely to have body odor associated with perspiration, and that the product should not be used on the face or neck (or the head in general, if desired), or on the hands.

Dispensers and Applicators

Any suitable known means may be used to dispense product from an applicator onto the skin. Antiperspirant formulations according to the various embodiments of the present invention can be provided in any suitable form such as a roll-on, a viscous hydrogel, a substantially solid gel, a spray (using an aerosol or pump), a lotion, a powder, a suspension, a wipe, a foam, etc. Delivery of active ingredients can be via any known method such as by spraying, wiping, extruding, pouring, rinsing, application with the fingers, etc., and combinations thereof.

In embodiments suitable for use with a roll-on dispenser, the dispenser may comprise a bottle having a mouth at one end defining a retaining housing for a rotatable member, such as a spherical ball or a cylinder which protrudes above the top wall of the bottle. Examples of suitable dispensers are described in EP1175165, "Package for Dispensing a Flowable Cosmetic Composition and Product," published Apr. 20, 2005 by Sima et al.; U.S. Pat. No. 6,511,243, "Container for Storing and Applying a Liquid Deodorant," issued Jan. 28, 2003 to Miranda; WO2006/007987, "Improvements in a Cosmetic Dispenser" and WO2006/007991, "Cosmetic Dispenser Housing and Method," both published Jan. 26, 2006 by Da Tavares et al.; all of which are herein incorporated by reference to the extent that they are noncontradictory herewith.

Stick forms of deodorants, for example, can include compressed powder sticks, gelled sticks, wax sticks and silicone sticks, such as the silicone formulations described in U.S. Pat. No. 5,888,486 issued Mar. 30, 1999 to Steinberg et al., previously incorporated by reference.

Stick deodorants and related cosmetic stick products are known in a variety of forms, all of which may be suitably adapted for the various embodiments described herein. For example, cosmetic sticks having antiperspirant and/or deodorizing effects and based on alcoholic soap gels and/or propylene glycol soap gels are well known (e.g., see U.S. Pat. No. 2,900,306, "Cosmetic and Deodorant Sticks," issued to Slater, August 1959; U.S. Pat. No. 2,857,315, "Propylene Glycol Soap Gel Stick Anti-Perspirant," issued October 1958 to Teller; and U.S. Pat. No. 2,933,433, "Stable Anti-Perspirant Stick," issued April 1960 to Teller et al.). A translucent stick product is described in U.S. Pat. No. 5,650,143, "Deodorant Cosmetic Stick Composition," issued Jul. 22, 1997 to Bergmann.

U.S. Pat. No. 3,576,776, herein incorporated by reference to the extent that it is noncontradictory herewith, describes adhesive applicator crayons where the gelling component is a salt formed by combining an aliphatic carboxylic acid having from 8 to 36 carbon atoms with a cation selected from alkali metals, ammonium and lower alkyl ammonium. This salt is added to water, either alone or in combination with a water-miscible organic solvent, producing a gel to which an adhesive component is added. The cation-carboxylic acid combination may be sodium stearate, for example. Further approaches are described in U.S. Pat. No. 4,252,789, "Deodorant Stick," issued Feb. 23, 1981 to Broad, herein incorporated by reference to the extent that it is noncontradictory herewith.

Other application means can include a foam applicator attached to a handle such as a tube or cylinder. In some embodiments, soft, flexible materials are used to transfer material from a container onto the skin. Such materials can include cloths such as terrycloth products or rags, sponges, puffs, wipes, and the like.

Preservatives and Antimicrobial Agents

Additional preservatives or antimicrobial agents may be provided in the formulations and systems described herein. Such agents may include cetylpyridinium chloride, parabens e.g., (methyl paraben, ethyl paraben), imidazolidinyl urea, propyl benzoate, sodium benzoatre, potassium sorbate, and the like. Other antimicrobial or bacteriostatic agents that may be considered include, by way of example only, biguanide, chitosan derivatives, silver nanoparticles or other silver-based compositions and products capable of releasing silver ions, and the like. Nisin, a polycyclic peptide antibacterial agent, may also be incorporate in some embodiments of the formulations of the present invention. Phytoextracts, essential oils, and related plant products with antimicrobial functionality may also be considered. Tea oil, for example, such as Melafresh T96 or SLR teal oils may be used.

Rheology Modifying Ingredients

Many known rheology modifiers can be considered in the formulations for the compositions of various embodiments to obtain desired properties. Gums such as guar gum or xanthan gum or other industrial gums, polyvinyl alcohols, polyacrylates, cellulose-derived polymers such as carboxymethylcellise or hydroxyalkylcellulose polymers, Laponite, clays, carboxomer polymers, and numerous other compounds can be considered. Silicone elastomers can be considered, including those described in U.S. Ser. No. 09/613,266 (P&G).

Known bioadhesive polymers may be used as part of the carrier system, including polyolprepolymers from Barnet Products Group (Englewood Cliffs, N.J.) and related compounds such as Barnet's Topicare® Delivery Compounds and related liquid polymers. Barnet's polyolprepolymers are polyalkalene glycol-based polyurethane polymers suitable for use as skin care agents that can hold active ingredients on the surface of the skin. They do not absorb substantially into the skin and can remain in place for a prolonged period of time, being capable of forming a liquid reservoir on the skin. Specific products include polyolprepolymer-2 (PP-2), polyolprepolymer-14 (PP-14), and polyolprepolymer-15 (PP-15). PP-2 is a lipophilic mixture of liquid hydroxy-terminated polymers in polypropylene glycol having oligomers with a molecular weight range of 1,500 to 10,000 and an average molecular weight of about 4,000 and an HLB in the range of 12-14. At 35° C., it has a reported viscosity of about 2500 to 4000 cps. PP-14 is similar but has a higher molecular weight of about 18,000 and is more lipophilic. It has an HLB of about 11-13. At 35° C., it has a reported viscosity of about 2500 to 6000 cps. PP-15 is a mixture of liquid hydroxy-terminated polymers in polyethylene glycol. It has a molecular weight of about 1,800 and is soluble in water and alcohol and can be used in aqueous systems with hydrophilic components. At 35° C., it has a reported viscosity of about 2500 to 5000 cps. See "Polyolprepolymers: Properties and Use in Cosmetic Products—Technical Manual," Bertek Pharmaceuticals, a subsidiary of Mylan Laboratories (Englewood Cliffs, N.J.), 1996.

The aforementioned polyolprepolymers are believed to be particularly useful in enhancing the efficacy of active ingredients such as alpha-hydroxy acids by holding them on the epidermis level and reducing irritation.

Skin Benefit Agents

Non-limiting examples of skin benefit agents that may be considered for use herein are described in *The CTFA Cosmetic Ingredient Handbook,* 2nd Edition (1992), which includes a wide variety of ingredients commonly used in the skin care industry, and which may be suitable for use in various embodiments of the present invention. Non-limiting examples of skin benefit agents include absorbents, aesthetic components such as fragrances, pigments, natural extractives such as witch hazel or aloe vera, colorings/colorants, essential oils, skin sensates, astringents, etc. (e.g., clove oil, menthol, camphor, eucalyptus oil, eugenol, menthyl lactate, witch hazel distillate), anti-caking agents, antimicrobial agents (e.g., iodopropyl butylcarbamate), antioxidants, colorants, cosmetic astringents, cosmetic biocides, drug astringents, external analgesics, opacifying agents, pH adjusters, skin-conditioning and/or moisturizing agents, i.e. glycerine, skin soothing and/or healing agents (e.g., panthenol and derivatives (e.g., ethyl panthenol), pantothenic acid and its derivatives, allantoin, bisabolol, and dipotassium glycyrrhizinate), retinoids, (e.g. retinol palmitate), tocopheryl nicotinate, skin treating agents, vitamins and derivatives thereof. It is to be understood that the actives useful herein can in some instances provide more than one benefit or operate via more than one mode of action. Therefore, classifications herein are made for the sake of convenience and are not intended to limit the active to that particular application or applications listed.

Moisturizers may include urea, which may also be used in combination with lactic acid for effective moisturizing activity.

Foam Embodiments

In some embodiments, the active ingredients are delivered to the body while in a foam state, such as stable foam, for example, that is produced with or without a propellant. In some versions, a foam is dispensed from a dispenser such as a propellant-free dispenser with pumping action to create the foam from a composition in a foamable carrier, and then applied to a wipe or other substrate, or applied to the hand of the user or otherwise delivered to the skin. Propellant-driving foam generators may also be used to deliver the composition in the form of a foam.

Active ingredients in a foam may be dispensed for subsequent placement on a dry wipe, a pre-moistened wipe, or other soft, flexible applicator (e.g., an object about 3-fingers wide or 4 to 10 cm wide) or other object to used for application of the foam-based composition to the skin. The foam can be a non-propellant foam. A foam with a suitable stiffness of yield stress can be applied to the skin in any manner for sustained adherence and contact with the body.

Examples of foam-based systems are described in U.S. Pat. No. 6,818,204, "Stable Foam for Use in Disposable Wipe," issued to Lapidus on Nov. 16, 2004, herein incorporated by reference to the extent that it is noncontradictory herewith. The Lapidus patent discusses the use of compatible surfactants, e.g., nonionic, anionic, amphoteric, for use in human hygienic products. The surfactant should be capable of forming a foam when mixed with air in a finger actuated, mechanical pump foamer. Such surfactants are said to include, without limitation, those which do not irritate mucous membranes such as polyethylene 20 cetyl ether (Brij 58)™, a nonionic surfactant; sodium lauroyl sarcosinate (Hamposyl L-30)™, sodium lauryl sulfoacetate (Lathanol LAL)™ and sodium laureth sulfate (Sipon ESY)™—anionic surfactants; lauramidopropyl betaine (Monateric LMAB™), an amphoteric surfactant, as well as polysorbate 20, TEA-cocoyl glutamate, disodium cocoamphodiacetate and combinations thereof. Typically, the surfactant is said to present in an amount from about 2% to about 35% by weight, or from about 5% to about 15% by weight.

At least one foam stabilizing agent may also be present in certain foamable embodiments. Suitable foam stabilizing agents may include, without limitation, natural or synthetic gums such as xanthan gum, polyalkylene glycols such as polyethylene glycol, alkylene polyols such as glycerine and propylene glycol and combinations thereof. Typically, the foam stabilizers may be present in an amount from about 0.10% to about 5%, or from about 2% to about 4%.

In the Lapidus patent (U.S. Pat. No. 6,818,204), alkylene polyols are said to be typically employed in amounts from about 0.1% to about 10%, gums are employed in amounts ranging from about 0.05% to about 1%, and/or polyalkylene glycols are present in amounts ranging from about 0.05% to about 2%.

A foam may be produced using the F2 Finger Pump Foamer™ manufactured by AirSpray International Inc. of Pompano Beach, Fla. Such a spring-loaded valve system operates without the use of gas propellants or the like. Upon actuation, precise amounts of air and liquid are mixed, and a foam capable of maintaining its structure for a substantial length of time is dispensed. In addition, the dispenser can deliver a variable amount of foam, thereby reducing waste of the wipe agent contained therein. Details of exemplary propellantless defoamers are described in U.S. Pat. No. 5,443,569, issued on Aug. 22, 1995, and U.S. Pat. No. 5,813,576, issued Sep. 29, 1998, herein incorporated by reference to the extent that it is noncontradictory herewith.

Other Ingredients

Many other ingredients may be used in the formulation provided they are not antagonistic to the intended function of the product. Such ingredients may include chelating agents such as EDTA, fragrances, viscosity modifiers, colors, opacifiers such as titanium oxide, sensory agents such as menthol or other known agents capable of producing a cooling or warming sensation on the skin; essential oils, fatty acids, proteins including various enzymes; probiotic agents to enhance growth of lactobaccili or other desirable bacteria, and the like.

Humectants and solubilizers may be used, such as butylene glycol.

In various embodiments, the formulation may be substantially free of any or all of the following: aluminum, aluminum salts, zirconium, zirconium salts, ethanol, methanol, propanol, alcohols, alcohols having 3 our fewer carbons, alcohols having 2 or fewer carbons, glycolic acid, acetic acid, critic acid, latex, spermicides, Octoxynol-9, TEA (triethylamine, a compound which may contribute to unwanted odor) or derivatives of TEA, TMA (trimethylamine), ammonia or complexes thereof, amines, protein, polyhydroxy fatty acids, polyhydroxy acids, alpha-hydroxy acids having 14 or greater carbons, fatty acids, polyhydroxy fatty acid esters (or polyhydroxy fatty acid derivatives such as esters, amides, and alcohols), benzoic acid, preservatives, perfumes, artificial colors, sodium bicarbonate, bicarbonates in solid or ionic form, retinol, or Retin-A. "Substantially free" in this context may mean lacking an effective quantity. For alcohols and acids this may be taken as less than 0.1%. In some cases, the concentration may be less than 0.05% or 0.01%. Xylitol or other 5-carbon sugars may be used to enhance the antimicrobial benefits of the composition.

The formulation may also comprise a plurality of other acidifying agents such as acetic acid, fumaric acid, ascorbic acid, and the like as well as buffers.

EXAMPLES

Example 1

A cream was formulated with a microsponge caffeine product for controlled released. Multiple product batches were made with the following target composition:
Mandelic acid 4-6%
Caffeine powder 3.0% (CapsuDar® Caffeine 85, a microencapsulated caffeine powder coated with cellulose derivative, marketed by LycoRed Bio Ltd. of Yavne, Israel).
Corn starch
Trichlosan
PP2 2.0% (Barnet Products Group, Englewood Cliffs, N.J.)
Aloe vera & chamomile
Tea tree oil
Other ingredients:
  Veg, glycerin
  Glyceryl stearate
  Cetyl alcohol
  Dimethicone
  Caprylic/Capric triglyceride
  Emulsifing wax
  Sodium hydroxide to PH 4.50
  Cucumber fragrance The cream was tested on several human users, using manual application to the underarm region and other areas as desired, with excellent results in controlling odor and reducing perspiration. Long-lasting odor control was observed, with several users indicating that successful antiperspirant performance increased initially as if the product performance was cumulative. With a week of daily use, significant reduction on odor was observed. Without wishing to be bound by theory, it may be that the cumulative effect over time is to substantially reduce the amount of odor-producing bacteria on the skin. The composition was also found to be effective in keeping body odor out of clothing also.

Users of this and related compositions observed that the skin felt smoother and was easier to shave, with less irritation. Without wishing to be bound by theory, it is believed that the alpha-hydroxy acids in this and related compositions act to smooth the skin and to soften hair, allowing shaving with less irritation.

This formulation appeared to work best if applied when the skin was dry.

Without wishing to be bound by theory, the corn starch appeared to play a useful role in absorbing moisture and providing a suitable body or viscosity to the formulation. A wide variety of starches may be considered, including starch modified to have cationic charge or other known natural or chemically modified starches. The starch may comprise from about 1% to about 80% of the composition, such as from about 5% to about 30% or from about 2% to about 20%, or greater than 10%.

Example 2

A viscous cream comprising lactic acid, mandelic acid, and an oil/water emulsion carrier was formulated using the following ingredients:

| | |
|---|---|
| Water | |
| Lactic acid | 8.0% |
| Mandelic acid | 4.0% |
| Glycerin | |
| Xanthan gum thickener | |
| Polyquaternium 10 | |
| Aloe vera extract | |
| Oat extract | |
| Allantoin | |
| Chamomile extract | |
| Sodium hydroxide | |
| Methylisothiazolinone (preservative) | |
| Capryl glycol | |

The pH of the formulation was 4.0.

This formulation was then tested as an odor control material for use on the pudendum with female subjects using an external test agency. Seventeen product summaries were collected from test subjects. The summaries are formatted on a 5 point scale with 5 being the most favorable to 1 being the least. The product was evaluated on the properties as follows, texture, feel after applied to the skin, irritability to the application area, reduction or blocked odor, how well the women liked the product and whether or not they would use the product again or recommend it to a friend. Most of the women fell between the ages of 20-50 with the exception on both extremes, the youngest being nineteen and the oldest aged sixty-five. One women was pregnant in her third trimester.

Each of 5 parameters are separately considered. All 17 gave the product a 5/5 rating in terms of texture and consistency.

The product was not irritating to the area of application. Thirteen of the 17 (76%) gave it a 5/5. Three of the 17 gave it a 4/5 or 18%. Combined 4-5/5 rating is 16/17 or 94%. One woman gave it a 3/5 rating and then explained that she had stinging upon initial application that went away quickly. She stated that overall the product worked and she would buy the product and use in the future. A point was made by several women that they had a warming sensation upon initial application that they felt meant it was working or one woman verbalized that it felt like K-Y warming gel. None of the women felt that this was a negative. Some said that they felt that it must be working.

The product reduced or blocked odor. Thirteen of the 17 (76%) gave the product a 5/5 rating for odor reduction. Three of the 17 gave a 4/5 or 18%. Combined rating of 4-5/5 is 16/17 or 94%. Of the women who gave a 4/5 in this category, there were no additional comments about why they felt it was less than a 5. One woman gave the product a 3/5. She said that it only made her feel more wet and she did not like the product. Others stated that they felt that the product helped with odor during menses, after intercourse or after working out.

For overall approval of the product, fourteen of the 17 (82%) gave it 5/5. One woman gave it a 4/5. Combined rating of 4-5/5 is 15/17 or 88%. One woman gave it a 2/5. (the one who did not like the product because it made her feel more wet). The same positive numbers were obtained when the subjects were asked if they would use this product again and recommend it to others.

The results demonstrate the utility of alpha-hydroxy acids in controlling the odor generation of bacteria present on the skin. Similar mechanisms may relate to the benefits related compositions have shown when used to control under-arm odor.

Example 3

Another version of a viscous cream was made with the following ingredients:

| | |
|---|---|
| Water | |
| Lactic acid | 10.0% |
| Safflower oil | |
| Mandelic acid | 2.0% |
| Tricontyl PVP (water proofing agent) | |
| Glyceryl Stearate | |
| PEG- 100 Stearate | |
| Emulsifing Wax | |
| Caprylic Capric Triglyceride | |
| Cetyl alcohol | |
| Dimethicone | |
| Polyacryamide | |
| C13 C14 Isoparaffin | |
| Laureth-7 | |
| Aloe vera | |
| Allantoin | |
| Oat extract | |
| Chamomile extract | |
| Sodium Hydroxide | |
| Phenoxyrthanol (preservative) | |
| Chlorphenensin (preservative) | |
| Benzoic acid (preservative) | |
| Sorbic acid (preservative) | |
| Butylene Glycol | |

Example 4

A composition for treating fishy odor arising from the pudendum was prepared using the ingredients and weight percents shown in Table 1:

| Sequence | INCI Names | Trade Names | % W/W | Suppliers |
|---|---|---|---|---|
| 1 | Water | D.I. Water | 49.60 | Open |
| 1 | Disodium EDTA | Versene Na2 | 0.100 | Open |

-continued

| Sequence | INCI Names | Trade Names | % W/W | Suppliers |
|---|---|---|---|---|
| 1 | Glycerin 99 vegetable | Glycerin 99 | 5.00 | Open |
| 1 | Lactic Acid 70% | Purac | 10.00 | Purac America |
| 1 | DL Mandelic acid | Mandelic Acid | 2.00 | Orient Star 310/ 7016402 |
| 1 | Allantoin | Allantoin | 0.10 | Open |
| 2 | Glyceryl Stearate & PEG 100 Stearate | Arlacel 165 | 3.50 | Open |
| 2 | Cetyl Alcohol | Cetyl Alcohol | 2.00 | Open |
| 2 | Dimethicone | Dow Corning 200/100 | 1.00 | Dow Corning |
| 2 | Caprylic/Capric Triglyceride | Liponate CG | 3.50 | Lipo chemical |
| 2 | Emulsifying Wax | Polawax | 3.00 | Croda |
| 2 | Tricontyl PVP | Ganez WP660 | 3.00 | ISP |
| 2 | Carthamus Tinctorius (safflower) Seed Oil | High oleic Safflower oil | 8.50 | Open |
| 3 | | Germazide PSB | 1.00 | |
| 3 | 50% Sodium Hydroxide | Sodium Hydroxide | 2.500 | Open |
| 3 | Aloe Barbadensis leaf extract | Aloe 10 Fold | 0.50 | Active organic |
| 3 | Avena Sativa (oat) kernel extract | Oat extract | 0.10 | Active organic |
| 3 | Chamomilla Recutita (Matricaria Matricaria) flower extract | Chamomile extract | 0.10 | Active organic |
| 4 | | Sepigel 305 | 2.50 | Seppic |
| 4 | PPG-12/SMDI Copolymer | Polyolperpolymer 2 | 2.00 | Barnet |

Procedures:
1. In a clean sanitized stainless steel tank, Sequence 1 ingredients were combined and mixed thoroughly to form a first mixture.
2. The first mixture was heated to 75° C. while mixing continued.
3. In a separate stainless steel tank, Sequence 2 ingredients were combined and heated to 75° C. to form a second mixture.
4. After slight cooling, when both mixtures were at 70° C., the second mixture was added gradually to the first mixture while mixing. Mixing continued for another 15 minutes to form a third mixture.
5. A cooling cycle was then started as the third mixture was cooled to 40° C. Then the Sequence 3 ingredients were added one at time in the listed order while mixing to form a fourth mixture.
6. The ingredients from Sequence 4 were then blended into the fourth mixture to form the final composition.

The final composition had a pH less than 4 and was then tested for efficacy, and was found to be effective in reducing fishy odor on the pudendum.

Example 5

A composition similar to that of Example 4 was produced, but with the additional presence of a prepolymer from Barnet Group, a described above. PP-2 was used. The resulting formulation was found to be surprisingly effective in preventing fishy odor from the pudendum, with a prolonged effect lasting over 24 hours. Without wishing to be bound by theory, it is believed that the prepolymer compound assists in holding the alpha-hydroxy acids of the composition off the skin and in an environment where they can be effective in maintaining a low pH and reducing the activity of anaerobic bacteria on the pudendum.

Example 6

In a prophetic example, 1% or greater caffeine by weight or other effective quantity of xanthine compounds are added to the caffeine-free formulations of Examples 2 through 5 to create a compound with the benefits of both xanthine compounds relative to sweat reduction and alpha-hydroxy acids relative to odor suppression. The product can then be formulated for a roll-on deodorant, a spray-on deodorant, a wipe, or a nonwoven or other absorbent pad that is worn under the arms that delivers and effective amount of the formulation to the skin under the arm.

Remarks

When introducing elements of aspects of the invention or the embodiments thereof, the articles "a," "an," "the," and "said" are intended to mean that there are one or more of the elements, and thus may include plural referents unless the context clearly dictates otherwise. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above compositions, products, and methods without departing from the scope of aspects of the invention, it is intended that all matter contained in the above description shall be interpreted as illustrative and not in a limiting sense.

While the foregoing description makes reference to particular illustrative embodiments, these examples should not be construed as limitations. The inventive system, methods, and products can be adapted for other uses or provided in other forms not explicitly listed above, and can be modified in numerous ways within the spirit of the present disclosure. Thus, the present invention is not limited to the disclosed embodiments, but is to be accorded the widest scope consistent with the claims below.

I claim:

1. A method for reducing body odor and perspiration on a user, comprising:
   a. preparing a personal care composition for reducing body odor comprising from 1.0% to 8.3% by weight of a methylxanthine or salts thereof and from 0.5% to 10% by weight of an alpha-hydroxy acid in a suitable carrier for application to the skin, wherein the personal care composition is in the form of a viscous compound selected from a cream, a lotion, a paste, or a slurry, the personal care composition comprising less than 0.5% by weight of zirconium and aluminum antiperspirant compounds, wherein the alpha-hydroxy acid comprises from six to twelve carbons;
   b. providing the personal care composition in packaging with indicia instructing the user to apply the personal care composition to a portion of the skin of a body of a user in order to reduce body odor and perspiration; and
   c. providing the personal care composition to the skin of the user.

2. The method of claim 1 wherein the alpha-hydroxy acid is mandelic acid.

3. The method of claim 1, wherein the viscous compound is provided in the form of a deodorant stick or a roll-on deodorant.

4. The method of claim 1 wherein the personal care composition comprises from 1.0% to 8.3% by weight of caffeine or salts thereof and the alpha-hydroxy acid comprises mandelic acid.

5. The method of claim 1 wherein the carrier is selected from an aqueous solution or an aqueous emulsion.

6. The method of claim 1 wherein the personal care composition comprises from 0.5% to 6% mandelic acid by weight and from 1.0% to 6% by weight of caffeine or salts thereof.

7. The method of claim 1 wherein the personal care composition is substantially free of trimethylamine and has a pH of 4.5 or less.

8. The method of claim 1 wherein the personal care composition further comprises at least 1% by weight of lactic acid.

9. The method of claim 1, wherein the viscous compound is provided in at least one of a wipe, an impregnated pad, a foam, a gel, or a cream.

10. A method for reducing underarm perspiration comprising:
    a. in a suitable carrier, forming a viscous compound by blending a methylxanthine compound with one or more alpha-hydroxy acid compounds comprising mandelic acid, wherein the concentration of the one or more alpha-hydroxy acid compounds in the viscous compound is from 0.5% to 10% by weight, and the concentration of the methylxanthine compound in the viscous carrier is at least 1%, and wherein the viscous compound comprises less than 0.5% by weight of zirconium and aluminum antiperspirant compounds;
    b. providing the viscous compound in a container;
    c. providing directions on the container or packaging thereof instructing a user to apply the viscous compound to the underarm area for the purpose of reducing perspiration and body odor; and
    d. applying the viscous compound to the underarm area of a user.

11. The method of claim 10, wherein the mass ratio of the alpha-hydroxy acid compound to the methylxanthine compound is greater than 1.

12. The method of claim 10, wherein the mass ratio of the alpha-hydroxy acid compound to the methylxanthine compound is greater than 1.2.

13. The method of claim 10, wherein the mass ratio of the alpha-hydroxy acid compound to the methylxanthine compound is from about 0.1 to about 1.

14. The method of claim 10, wherein the mass ratio of the alpha-hydroxy acid compound to the methylxanthine compound is from 1 to 5.

15. The method of claim 10, wherein the mass ratio of the alpha-hydroxy acid compound to the methylxanthine compound is from 0.1 to 5, and wherein methylxanthine compound is caffeine or salts thereof.

16. A method of reducing body odor and perspiration on the body of a user comprising:
    a. preparing an personal care composition in a suitable carrier for application to the skin comprising at least one of water and/or an alcohol, the personal care composition comprising from 1.0% to 8.3% by weight caffeine or salts thereof and from 1% to 10% by weight of mandelic acid, wherein the personal care composition comprises less than 0.5% by weight of aluminum and zirconium antiperspirant compounds;

b. packaging the personal care composition in a suitable container for use as an underarm antiperspirant, wherein the personal care composition when applied to the skin is effective as an antiperspirant;
c. providing indicia associated with the personal care composition instructing a user to apply the personal care composition to a portion of the body commonly associated with unwanted body odor and perspiration to reduce body odor and perspiration; and
d. applying the personal care composition to said portion of the body of a user.

17. The method of claim 16 wherein the packaging for the personal care composition comprises at least one of a spray can, spray bottle, a foam dispenser, a squeezable tube, a pump dispenser, a tub, or a roll-on deodorant dispenser.

18. The method of claim 16 wherein the personal care composition is provided in the form of a deodorant stick or a roll-on deodorant.

19. The method of claim 17, wherein the indicia further direct the user to apply the personal care composition to region of the body with apocrine sweat glands and to apply the personal care composition repeatedly at spaced apart intervals.

20. The method of claim 17, wherein the personal care composition further comprises starch and at least 1% by weight of lactic acid, and is substantially free of trimethylamine.

* * * * *